(12) United States Patent
Wessel et al.

(10) Patent No.: US 6,511,566 B1
(45) Date of Patent: Jan. 28, 2003

(54) METHOD OF PRODUCING A FIBROUS MATERIAL LAYER

(75) Inventors: Peter Wessel, Ytterby (SE); Urban Nilsson, Hålta (SE); Kent Edgren, Mölnlycke (SE); José-Maria Mansisidor, Mölnlycke (SE); Dragoljub Kustrimovic, Göteborg (SE)

(73) Assignee: SCA Hygiene Products AB, Gothenberg (SE)

( * ) Notice: Subject to any disclaimer, the term of this patent is extended or adjusted under 35 U.S.C. 154(b) by 0 days.

(21) Appl. No.: 09/204,540

(22) Filed: Dec. 3, 1998

(30) Foreign Application Priority Data

Dec. 3, 1997 (SE) .............................. 9704484
Jul. 13, 1998 (SE) .............................. 9802517

(51) Int. Cl.[7] .............................................. D04H 3/14
(52) U.S. Cl. .................... 156/181; 156/209; 156/73.1; 156/73.2; 604/358; 604/367; 604/385.23; 428/156; 19/65 T; 19/299; 28/282
(58) Field of Search .................... 156/181, 209, 156/296, 73.2, 73.5, 73.1, 180, 166; 604/385.1, 358, 359, 367, 370, 365, 366, 378, 383, 385.23; 428/58, 114, 156; 19/65 T, 299

(56) References Cited

U.S. PATENT DOCUMENTS

| 3,371,667 A | | 3/1968 | Morse | |
|---|---|---|---|---|
| 3,430,295 A | | 3/1969 | Dixon | |
| 3,535,745 A | | 10/1970 | Zeidman | |
| 3,802,980 A | * | 4/1974 | Harmon | 156/181 |
| 4,334,340 A | * | 6/1982 | Reba | 19/299 |
| 4,340,563 A | * | 7/1982 | Appel et al. | 264/518 |
| 4,360,022 A | * | 11/1982 | Usami et al. | 128/290 |
| 4,435,239 A | * | 3/1984 | Harris | 156/180 |
| 4,685,914 A | * | 8/1987 | Holtman | 604/368 |
| 5,128,193 A | * | 7/1992 | Anapol et al. | 428/171 |
| 5,146,651 A | * | 9/1992 | Duffy et al. | 19/65 T |
| 5,382,245 A | | 1/1995 | Thompson et al. | |
| 5,466,513 A | * | 11/1995 | Wanek et al. | 428/218 |
| 5,620,641 A | * | 4/1997 | Berger | 264/103 |
| 5,626,571 A | * | 5/1997 | Young et al. | 604/370 |
| 5,669,895 A | | 9/1997 | Murakami et al. | |
| 5,677,058 A | * | 10/1997 | Neal et al. | 428/375 |
| 5,810,800 A | * | 9/1998 | Hunter et al. | 604/385.2 |
| 5,951,535 A | * | 9/1999 | Fujiwara et al. | 604/384 |
| 6,053,999 A | * | 4/2000 | Marcus | 156/73.2 |
| 6,069,097 A | * | 5/2000 | Suzuki et al. | 442/328 |
| 6,127,593 A | * | 10/2000 | Bjorkquist et al. | 604/364 |
| 6,166,285 A | * | 12/2000 | Schulte et al. | 604/364 |

FOREIGN PATENT DOCUMENTS

| EP | 0 391 814 A2 | 10/1990 |
|---|---|---|
| EP | 0 474 777 A1 | 2/1993 |
| EP | 0 312 118 B1 | 2/1996 |
| GB | 1137870 | 12/1968 |
| GB | 2 209 672 | 5/1989 |
| WO | WO 93/09745 | 5/1993 |

* cited by examiner

Primary Examiner—Michael W. Ball
Assistant Examiner—Jessica Rossi
(74) Attorney, Agent, or Firm—Burns, Doane, Swecker & Mathis, L.L.P.

(57) ABSTRACT

Method of producing a fibrous material layer mainly intended to be incorporated in an absorbent article such as a diaper, pant diaper, incontinence guard, sanitary napkin or the like. At least one bundle of continuous filaments, so called tow (12), is opened and the filaments are separated and evened to a layer having the desired fiber distribution, after which the layer is bonded in points, spots or lines in a bonding pattern, but where the filaments otherwise are substantially unbonded to each other.

23 Claims, 8 Drawing Sheets

METHOD OF PRODUCING A FIBROUS MATERIAL LAYER

TECHNICAL FIELD

The present invention refers to a method of producing a fibrous material layer mainly intended to be incorporated in an absorbent article such as a diaper, pant diaper, incontinence guard, sanitary napkin or the like.

BACKGROUND OF THE INVENTION

Absorbent articles of the above mentioned kind are intended to absorb body liquids such as urine and blood. They usually comprises a liquid pervious topsheet, intended to be facing the wearer during use, in the form of a nonwoven material for example a spunbond material. It is also known to incorporate a liquid acquisition layer between the topsheet and the absorbent body, said liquid acquisition layer having the ability to quickly receive large amounts of liquid, to distribute it and temporarily store it before it is absorbed by the underlying absorbent body. This is important especially in today's thin compressed absorbent bodies often with a high amount of so called superabsorbents, which have a high absorption capacity but in many cases a too low absorption speed in order to momentaneously be able to absorb the large amount of liquid that can be discharged during a few seconds at urination.

A porous relatively thick acquisition layer, for example in the form of a fibrous wadding, a carded fibrous web or other type of fibrous material has a high momentaneous liquid receiving capacity and can temporarily store liquid before it is absorbed by the absorbent body. The same applies for porous foam materials. The liquid is then drained successivley to the underlying absorbent body, after which the acquisition layer again has capacity to receive liquid from a repeated wetting.

Examples of absorbent articles comprising such porous acquisition layer are for example disclosed in U.S. Pat. No. 3,371,667, EP-A-0,312,118 and EP-A-0,474,777.

The materials used today as acquisition layers in absorbent articles are mostly functioning well but are relatively expensive and can sometimes have an insufficient acquisition time, especially at the second and third wettings if large amounts of liquid are involved.

It is previously known through EP-A-0,391,814 and GB-B-2,209,672 to use continuous nonbonded synthetic fibers, so called tow, in absorbent articles to spread liquid in the longitudinal direction of the article.

Another problem is that conventional liquid pervious topsheet materials used for absorbent articles of this kind, usually a nonwoven material of synthetic fibers, e g a spunbond material, often has a lower acquisition rate for liquid than the acquisition layer, at which liquid can leak from the article before it reaches the acquisition layer. The problem can of course be solved by using a topsheet material which is very open and by that has a high liquid permeability. Such an open topsheet material can however cause problems with a too low strength and sharp fiber ends from the acquisition layer may penetrate the open topsheet material and irritate the user.

OBJECT AND MOST IMPORTANT FEATURES OF THE INVENTION

The object of the present invention is to provide a method of producing a fibrous material layer having a high acquisition rate for liquid also at repeated wettings, has a high strength and wear resistance, high comfort and can be produced at a low cost. The method should besides be adapted to high production speeds. This has according to the invention been provided by taking at least one bundle of continous filaments, so called tow, which is opened and the filaments are separated and evened to a layer having the desired fiber distribution, after which the layer is bonded in points, spots or lines in a bonding pattern, but where the filaments otherwise are substantially unbonded to each other.

Further features of the invention are evident form the following claims and from the description.

The material layer can be used as a liquid acquisition layer under a topsheet material, as a topsheet material or as an integrated topsheet/liquid acquisition layer.

DESCRIPTION OF THE DRAWINGS

The invention will below be closer described with reference to some of the embodiments shown in the accompanying drawings.

DESCRIPTION OF EMBODIMENTS

Figure 1:
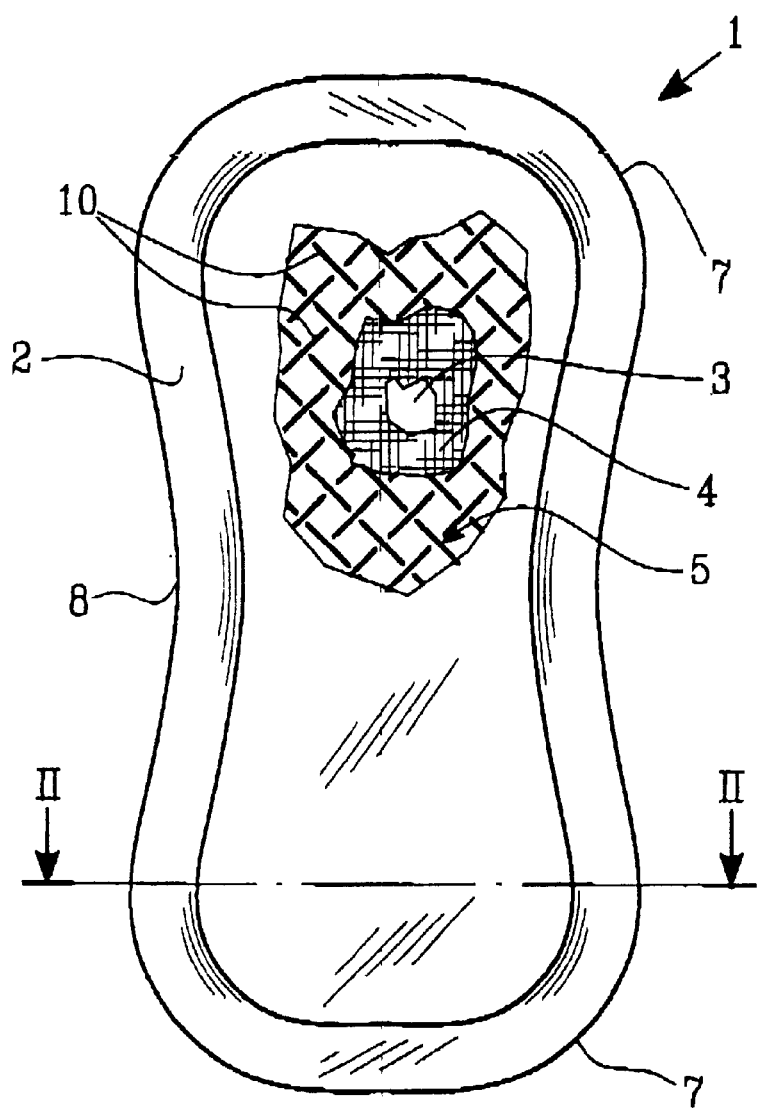
FIG. 1 is a plan view of an absorbent article in the form of an incontinence guard.
Figure 2:
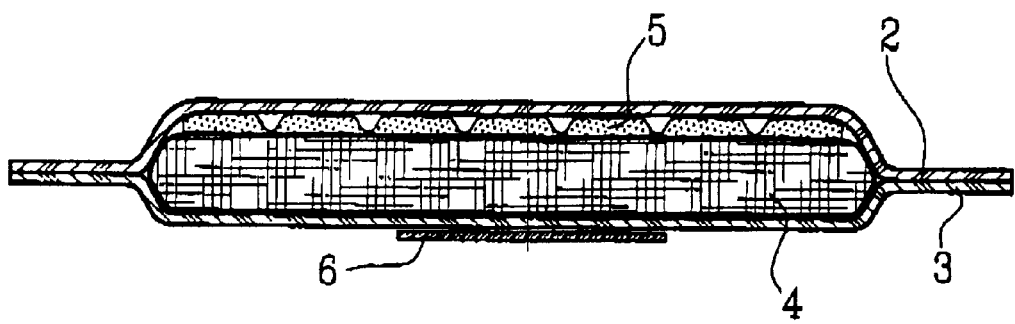
FIG. 2 is a section according to the line II—II in FIG. 1.

FIGS. 1 and 2 show schematically an example of an incontinence guard 1 comprising a liquid pervious topsheet 2, a liquid impervious backsheet 3 and a absorbent body 4 enclosed therebetween. A porous resilient liquid acquisition layer 5 is arranged between the liquid pervious topsheet 2 and the absorbent body 4.

The liquid pervious topsheet 2 can comprise a nonwoven material, for example a spunbond material of synthetic filaments, a meltblown material, a thermobonded material or a bonded carded fibrous material. The liquid impervious backsheet 3 can consist of a plastic film, a nonwoven material which is coated with a liquid impervious material or a hydrophobic nonwoven material which resists liquid penetration.

The topsheet 2 and the backsheet 3 have a larger surface area than the absorbent body 4 and the liquid acquisition layer 5 and extend outside the edges thereof. The layers 2 and 3 are interconnected within the projecting portions, for example by gluing or welding with heat or ultrasonic.

The absorbent body 4 can be of any conventional kind. Examples of common absorption materials are cellulosic fluff pulp, tissue layers, highly absorbent polymers (so called superabsorbents), absorbent foam materials, absorbent non-woven materials and the like. It is common to combine cellulosic fluff pulp with superabsorbents in an absorbent body. It is also common to have absorbent bodies comprising layers of different materials with different properties concerning liquid acquisition capacity, liquid distribution capacity and liquid storage capacity. This is wellknown for the person skilled in the art and need not be described in detail. The thin absorbent bodies which are common in for example baby diapers and incontinence guards often consist of a compressed mixed or layered structure of cellulosic fluff pulp and superabsorbent.

On the outside of the liquid impervious backsheet 3 fastening means in the form of strips 6 of a selfadhesive glue are arranged. An incontinence guard of the kind shown in FIG. 1 is mainly intended to be used by persons suffering from a relatively light incontinence and is easily worn in ordinary underpants. The fastening means 6 serve to keep the incontinence guard in place in the underpants during use. A number of other types of glue patterns, for example transverse, are of course possible as well as other types of fastening means such as hook and loop, snap fasteners, girdles, special underpants or the like.

The incontinence guard is hour glass shaped with broader end portions 7 and a more narrow crotch portion 8 located between the end portions. The crotch portion 9 is the portion of the incontinence guard that is intended during use to be worn in the crotch between the legs of the wearer and serve as a receiving portion for the discharged body fluid.

It should be noted that the incontinence guard shown in the drawings and described above only is a non-limiting example of an absorbent article. Thus the shape of the article as well as the construction thereof can be varied. The absorbent article can also be a diaper, a pant diaper, a sanitary napkin or the like. The absorbent article can be disposable or reuseable. For reuseable articles other materials than the above described are however used as a liquid pervious topsheet and absorbent body respectively.

Between the liquid pervious topsheet 2 and the absorbent body 4 there is arranged a porous and resilient acquisition layer 5 having the ability to quickly receive large amounts of liquid and distribute the liquid and store it temporarily before it is absorbed by the underlying absorbent body 4. This ability should be essentially maintained also after wetting of the material. The acquisition layer 5 can either cover the entire absorbent body 4, extend outside thereof or cover only part of the central portions of the absorbent body.

According to the invention the acquisition layer 5 consists of a layer of continuous fibers 9, so called tow, which have been bonded together in points, spots or lines forming a bonding pattern 10, but otherwise are substantially unbonded to each other. In the embodiment shown in FIG. 1 the bonding pattern 10 is a pattern of lines with short lines arranged in a zigzag configuration. The bonding pattern is achieved by for example ultra sonic welding or other thermal bonding. Examples of other suitable thermal bonding methods are pattern calendering, laser bonding etc. This implies that at least some of the fibers in the tow are thermoplastic. Examples of thermoplastic fibers are polyolefines, polyamides, polyester and the like. Also so called bicomponent fibers are included. As an alternative to thermobonding bonding can be made by a bonding agent through so called print bonding or dotbonding or mechanically through so called entangling by needling or by water jets. The choice of bonding type is mainly decided by which type of fibers are used in the tow.

The design of the bonding pattern 10 can of course vary within wide limits. The pattern may be in the form of points, spots or preferably lines. The lines may be straight as well as curved and the length can vary from a few millimeters to extending transversely or diagonally across the entire article. Preferably the lines extend across or obliquely across the longitudinal direction of the fibers 9, so that a plurality of fibers are bonded to each other by each bonding line. It is also an advantage if different bonding lines overlap each other as seen across the longitudinal direction of the fibers, so that a main part of the fibers are bonded at least at some part of their length.

The bonding pattern can be the same over the entire acquisition layer 5 or be different in different parts thereof, thus the bonding pattern can be more sparse in the wetting area and tighter outside thereof It is also possible to design the bonding pattern in such a way that the layer 5 will have different thickness in different parts of the article, for example thinner in the central portions thereof and thicker in the surrounding edge portions in order to create a bowl shape which provides a liquid receiving volume, alternatively thicker in the central portions than in the surrounding edge portions in order to provide a better body contact.

Figure 3:
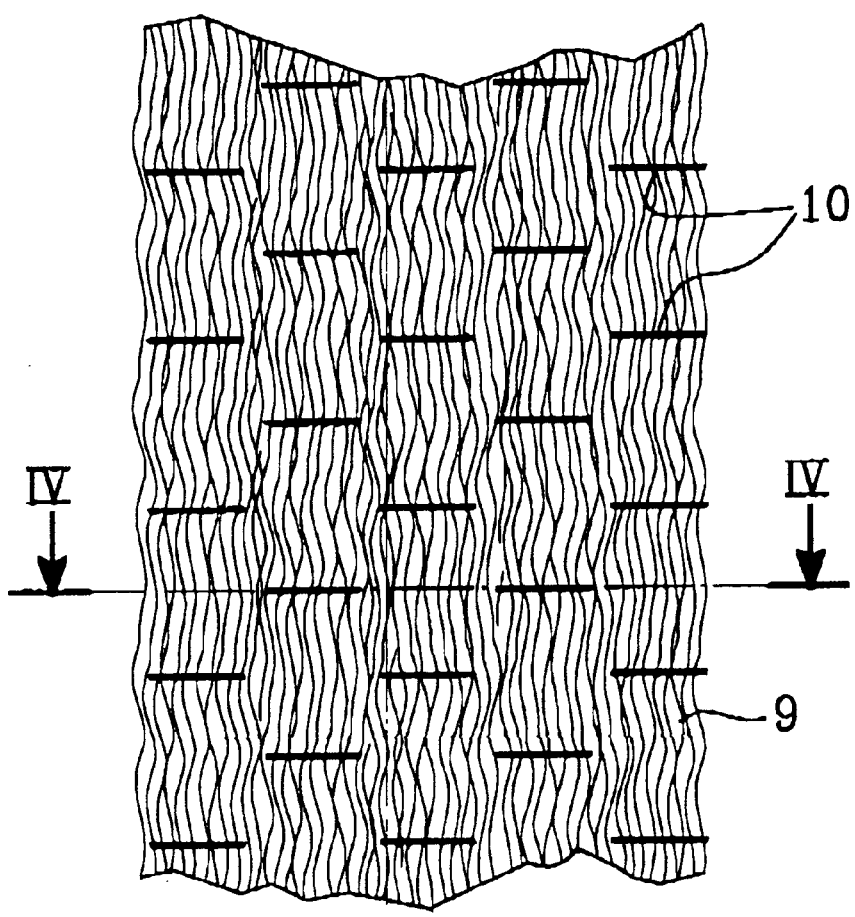
FIG. 3 shows schematically a piece of a fibrous material layer according to the invention.
Figure 4:
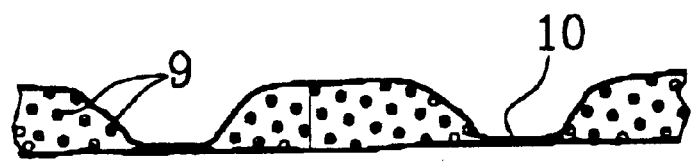
FIG. 4 shows on an enlarged scale a section according to the line IV—IV in FIG. 3.

In FIGS. 3 and 4 there are schematically shown a piece of a layer 11 of continuous fibers 9 which have been bonded in a simple bonding pattern 10 with transverse short lines. The fibers 9 are except at the bonding sites unbonded to each other.

The layer 11 of continuous fibers 9 according to the invention can besides as a liquid acquisition layer in an absorbent article be arranged as a topsheet material closest to the wearer or as a combined topsheet/acquisition layer. It can also be bonded to a carrier material, for example a nonwoven.

Figure 5:
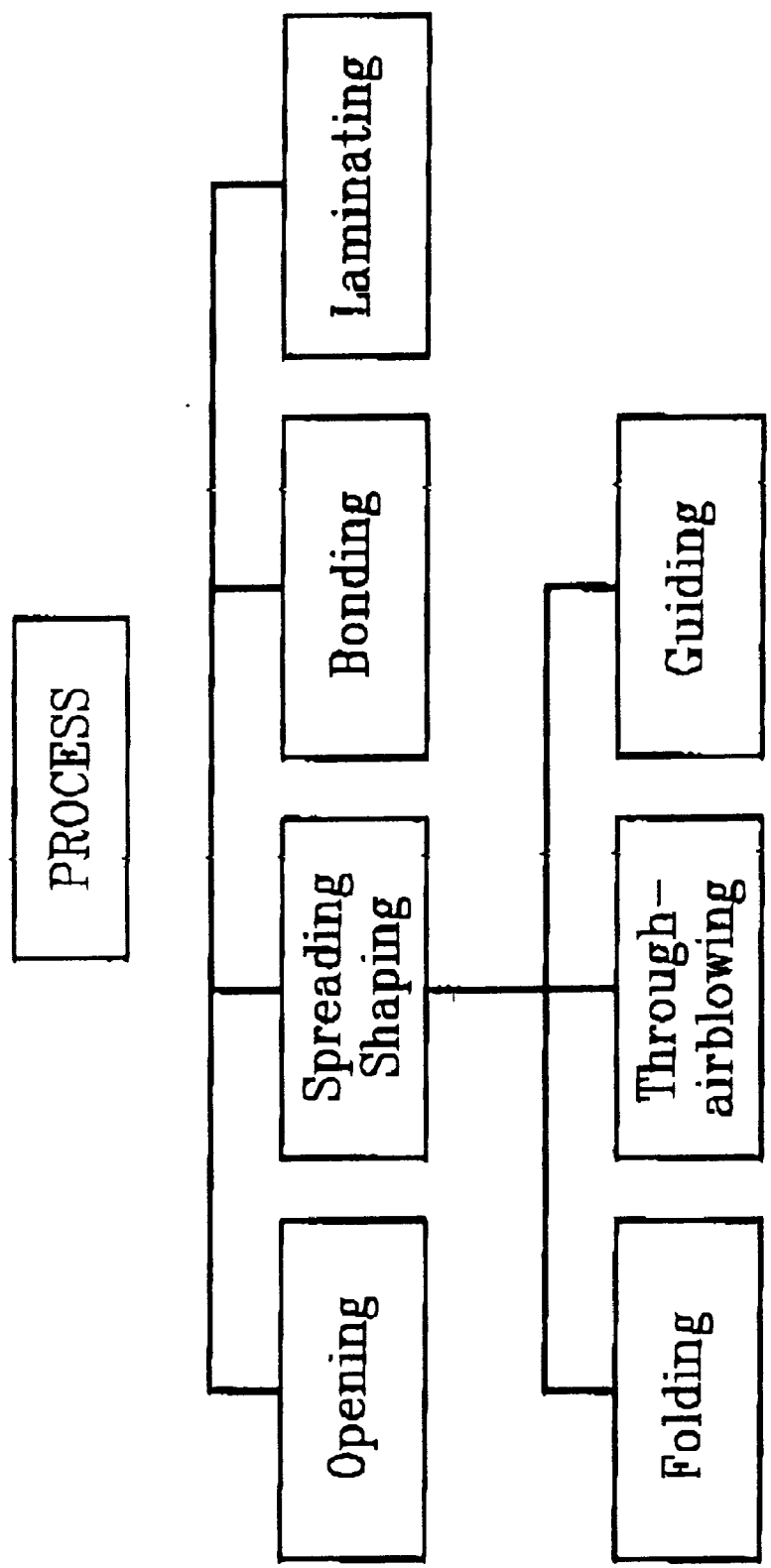
FIG. 5 shows schematically in the form of a block diagram the different main steps of the method according to the invention.
Figure 6:
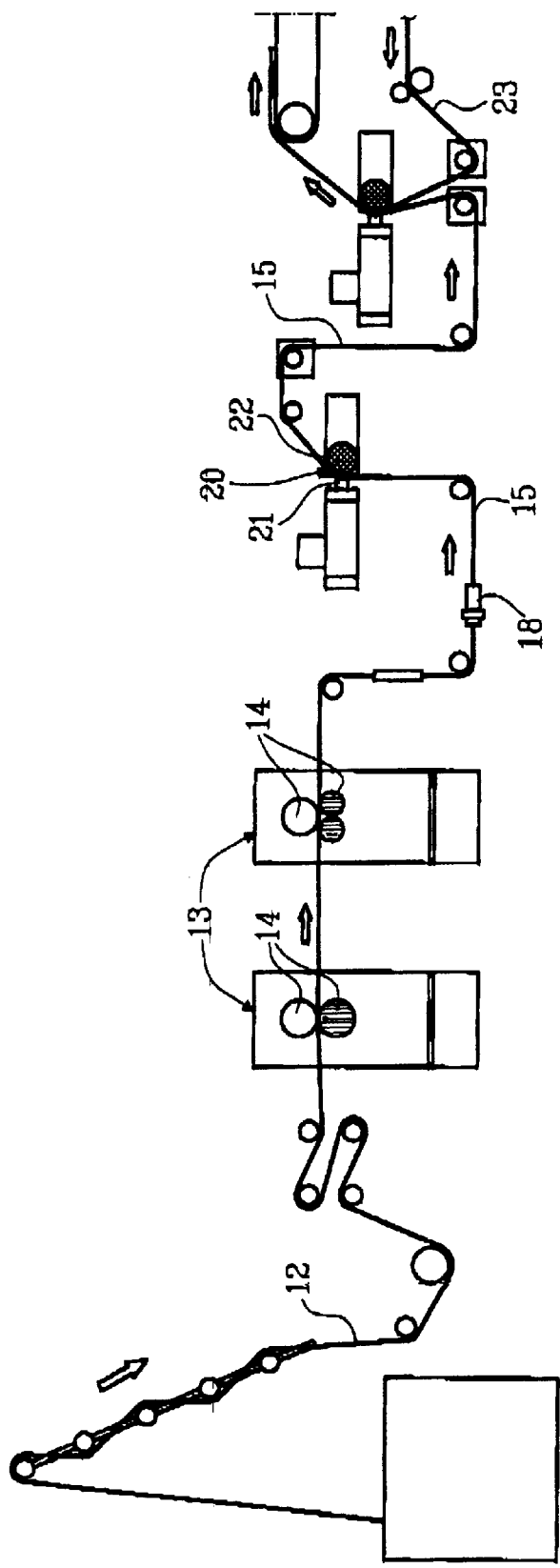
FIG. 6 is a schematic side view of a process equipment for performing the method according to the invention.
Figure 7:
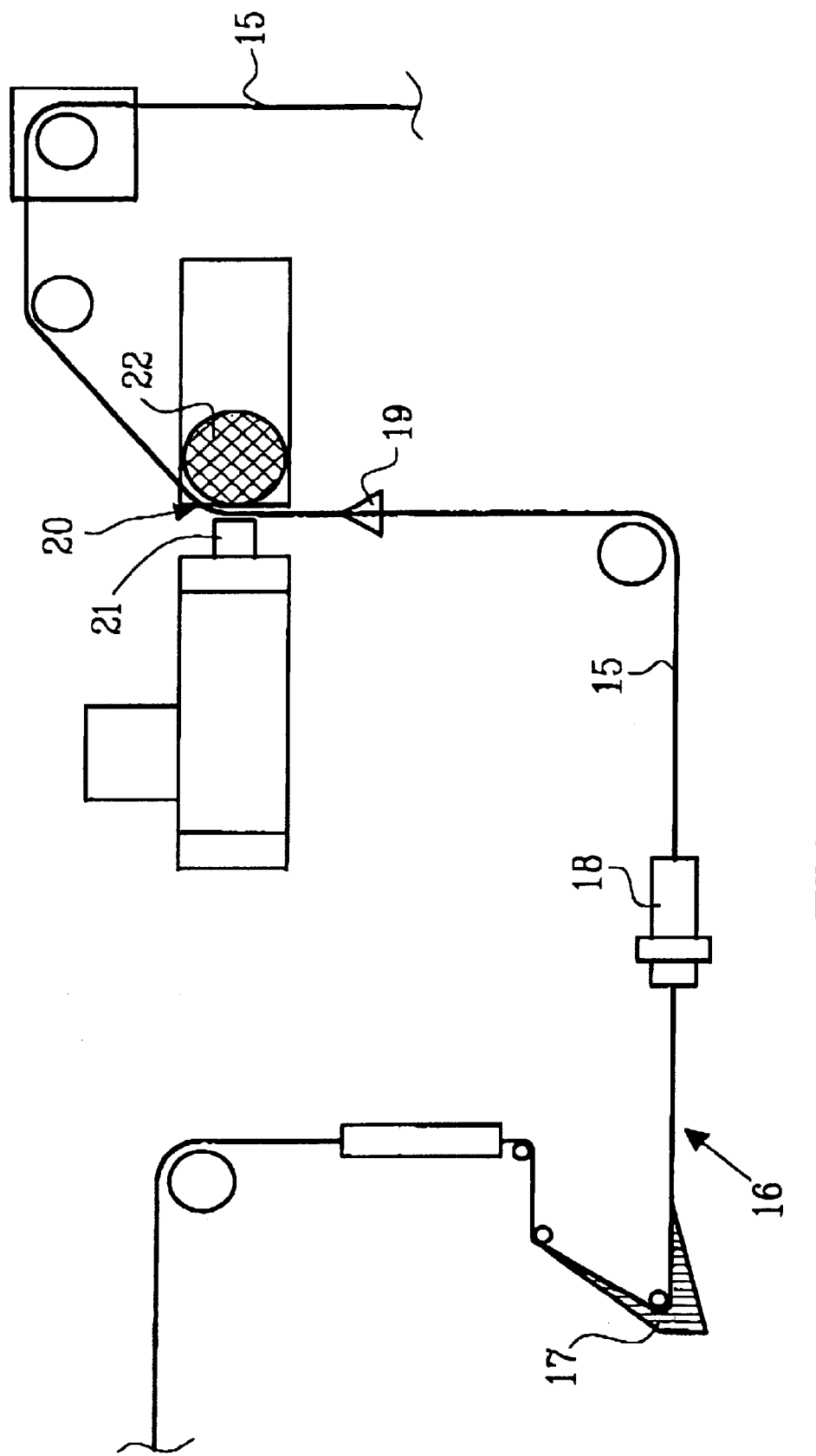
FIG. 7 shows a schematic side view of a modified embodiment of the equalizing device included in the process equipment.

The method of producing the material layer according to the invention comprises several steps, which is schematically illustrated in FIGS. 5, 6 and 7. Fiber tow 12 is supplied in sacks or in the form of bales or rolls of continuous fibers, which either are straight, crimped or curled. Crimped or curled fibers are preferred in this case since they provide a very open and airy structure. The fibers in the tow can be of any suitable material such as polyethylene, polypropylene, polyamide, polyester, polylactide, polyvinyl acetate, cellulose acetate, regenerated cellulose such as viscose and rayon, or af bicomponent type with a shell of a polymer having a lower melting point and a core of a polymer having a higher melting point. Specially preferred are such fibers having a high resiliency, for example polyester, copolyester and polypropylene.

The fiber thickness can vary but should be in the interval 0.5 to 10 dtex, preferably 1.5 to 25 and most preferably 2–15 dtex, if the material is to be used as an acquisition layer. The open airy structure in combination with the relatively coarse fiber dimension gives a very rapid liquid acquisition. Besides the material is strong due to the continuous fibers which provide strength in the longitudinal direction, and the bonding pattern which provides strength in the transverse direction.

The bales or the like are opened in special opening equipments in which the fibers are separated from each other, stretched and spread out to an essentially evenly thick layer. The layer is bonded in the desired bonding pattern according to above and is cut in suitable lengths either before or after application in an absorbent article. The bonding can alternatively be made after cutting. A tow is a relativley cheap delivery form of fibers as compared to nonwoven, waddings or the like which are normally used as acquisition materials.

As can be seen from FIG. 6 the opening device 13 comprises one or more pairs of rolls forming a roll nip, said rolls either being smooth or one roll is threaded and the opposite roll is a counter roll, the fiber tow being fed through said roll nip(s), which provides a separation of the fibers. The fibers are stretched during their passage through the roll nip(s) 14. This type of opening devices are of conventional kind and are available on the market in different constructions.

Figure 8:
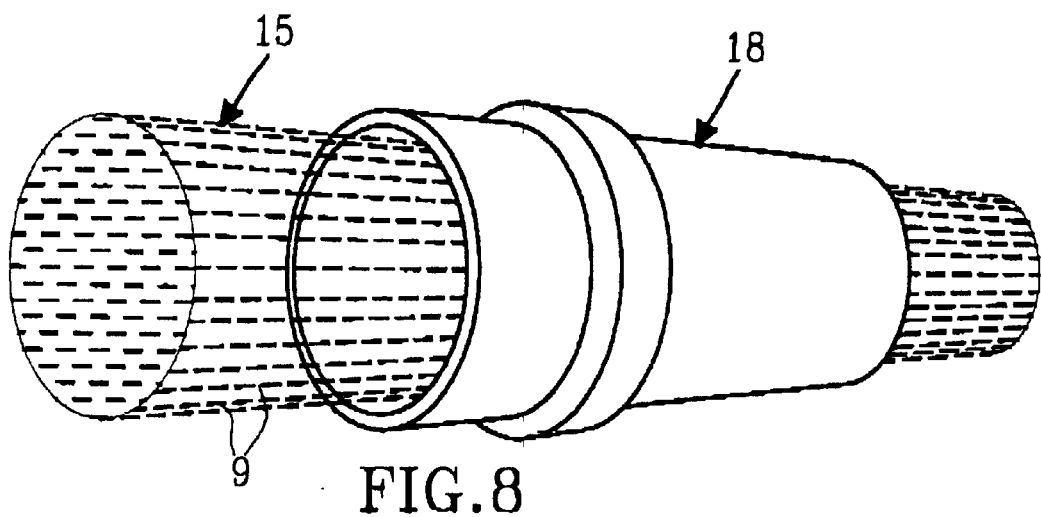
FIG. 8 shows schematically the feeding of the fibrous layer through en ejector.

According to the embodiment shown in FIG. 6 the opened fiber tow, which now is in the form of a spread-out layer of separated individual fibers 9, is led through an ejector 18 which blows air into the material web 15 substantially in the longitudinal direction thereof. This through-air blowing is important for achieving the desired volume and bulkiness of the material web. In FIG. 8 there is schematically shown the feeding of the material web 15 through the ejector 18. The material is fed through the ejector 18 which in an enclosed chamber blows air across and along the material as seen in the feeding direction thereof. By this there is achieved an increased mixing of the fibers which leads to that each fiber will be less dependent on the adjacent fibers. The fluffiness of the material web is markedly increased, especially if the fibers are crimped or helically curled. The flowing of air through the material web, which either is made along, across or obliquely across the feeding direction of the material web, can be achieved in other ways than by an ejector, e g by means of a so called air knife. A flowing of air across the material web contributes to evening or equalizing thereof.

Figure 10:
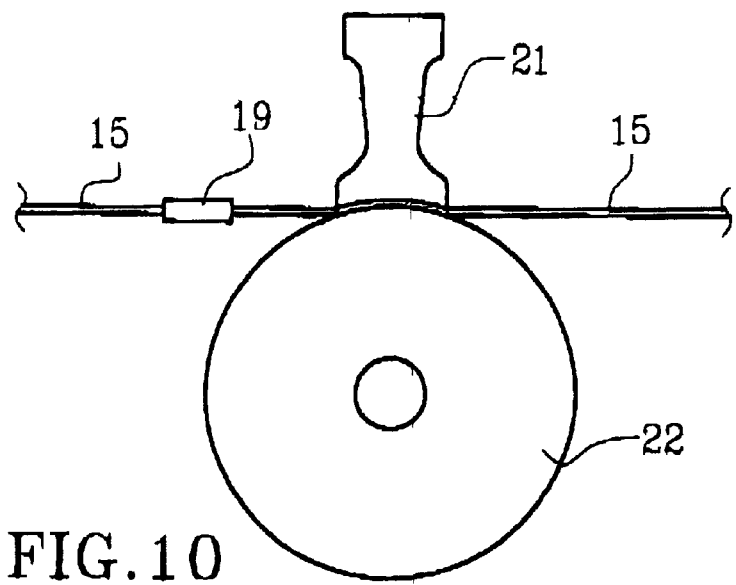
FIG. 10 shows a schematic side view of the feeding of the material layer towards the bonding station, in this case an ultrasonic welding device.

The material web 15 is then fed to a bonding station 20, which in this embodiment is an ultra sonic welding device. This comprises an ultra sonic horn 21 arranged just opposite a pattern roll 22 (FIG. 10).

Figure 11A:
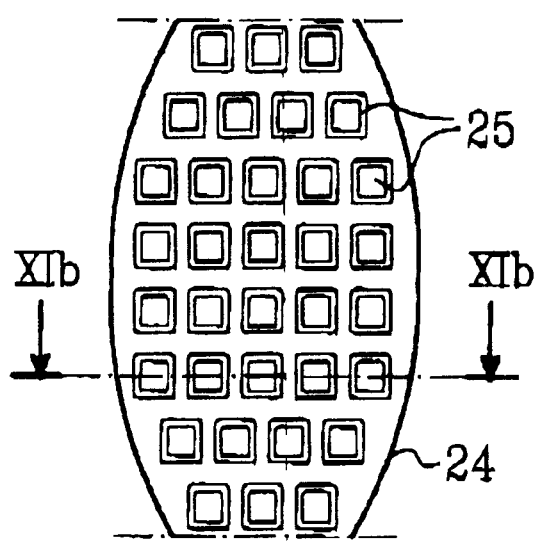
FIG. 11 shows schematically on an enlarged scale a special configuration of the pattern on the ultrasonic welding device for providing the bonding pattern.
Figure 11B:
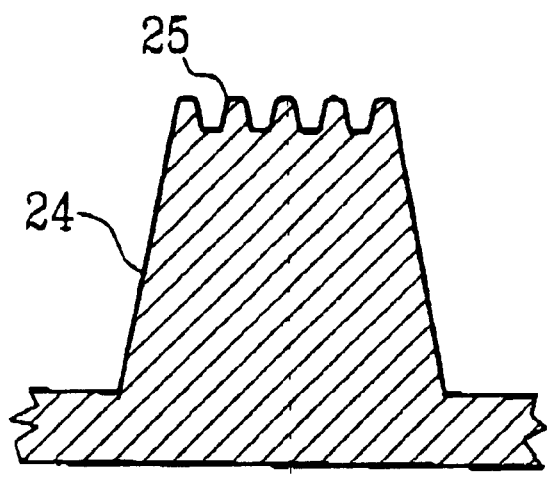

The pattern roll 22 can besides a macropattern, e g a pattern of lines or other optional pattern, be provided with a micropattern, an uneven or grooved surface, on the top surface of the protruded parts 24 of the pattern roll 22, which form the macropattern. This is shown in FIG. 11 of the drawings, at which the macropattern is denoted 24 and the micropattern is denoted 25.

By the micropattern the total welding surface is divided in smaller parts, at which there will be less material to melt and the friction between the material web and the ultrasonic welding device is reduced. The height of the micropattern is of the magnitude tenth parts of a millimeter, this applies also for their length and width. The micropattern makes it possible to weld at higher speeds without risk that the joint breaks during bonding. It would also be possible to weld an uneven material web, i e in which the material thickness varies across the machine direction.

It would also be possible to have an uneven or grooved surface on the ultrasonic horn 21.

As is mentioned above other types of thermal bonding methods than ultrasonic welding can be used, such as pattern calendering, laser bonding etc. As an alternative to thermal bonding bonding can be made by means of a bonding agent, so called printbonding or dotbonding or mechanically by so called entangling by means of needles or water jets.

The material web 15 can possibly after the pattern bonding be laminated to a nonwoven material 23 or a plastic film, which may be perforated or breathable, by thermobonding, e g ultrasonic welding or by a bonding agent, e g a glue. The nonwoven material 23 or the like can either be laminated to the material web 15 over the entire width thereof or in the form of strips be laminated only to the edges of the material web. The nonwoven material 23 or the like, which is either hydrophobic or hydrophilic, serves to prevent spreading of liquid toward the edges of the absorbent article and to prevent rewetting of liquid towards the skin of the wearer.

The pattern bonded material web 15, which optionally has been laminated to a nonwoven material or the like, can then either be wound on a winding roll or directly fed into a diaper machine or the like, where it is applied as a layer in an absorbent article such as a diaper, a pant diaper, an incontinence guard, a sanitary napkin or the like.

According to the embodiment shown in FIG. 7 one or more folding devices 17 are arranged before the ejector 18, the material web 15 being longitudinally folded one or more times in said folding device(s). The folding device 17 preferably consists of a guiding plate which forces a part of the material web 15 to be folded over a part or the rest of the material web. This folding can be made in different ways, such a double folding, in which half of the material web is folded over the other half, folding from two directions, in which a part of the material web's both edges are folded over the rest or a part of the rest of the material web, or overlap folding, in which the material web is folded from both directions in such a way that the folded portions of the material web overlap each other in the mid portion of the material web. This folding of the material web 15 is appropriate in such cases where the material web after the opening device has an uneven fiber distribution, which can be evened by folding the material web.

It is also possible to control the fiber distribution of the material web 15 having passed the folding device 17 by the folding method used. It would thus be possible to obtain a material web having an essentially even fiber distribution in the transverse direction or a material web having a varying fiber distribution in the transverse direction, either a greater thickness in the mid portion or along the edges.

After the folding device 17 an ejector 18 is arranged as described above.

A further control of the fiber distribution in the transverse direction of the material web is obtained according to the embodiment shown in FIG. 7 in a guiding device having a certain cross sectional shape, e g a funnel 19, through which the material web 15 is fed before it is fed towards the bonding station 20. The cross sectional shape of the funnel 19 thus decides the fiber distribution and by varying the shape of the funnel one can obtain a desired width of the material web and a desired distribution of the thickness of the material web 15 in its cross direction before it is bonded in the bonding station 20.

Figure 9A:
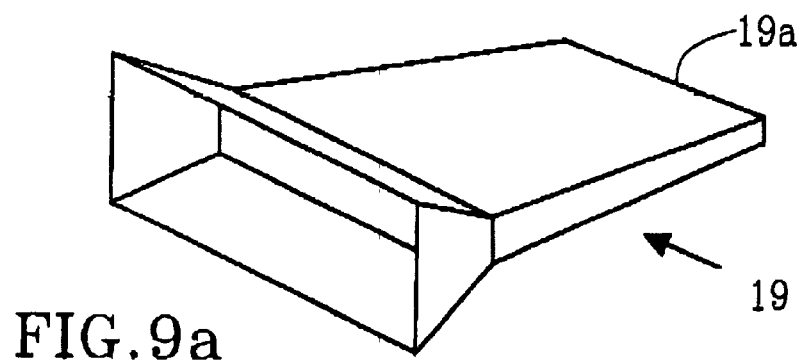
FIGS. 9a–d show some variants of the guiding means included in the equalizing device.
Figure 9B:
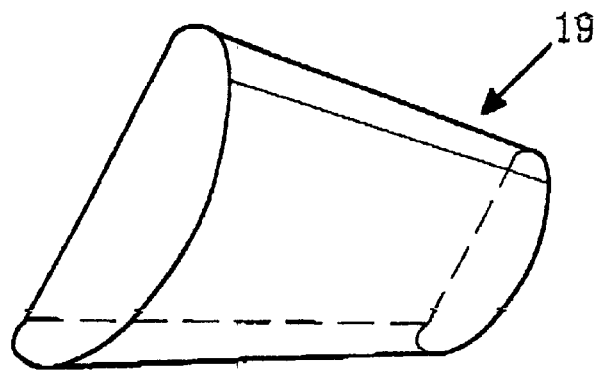
Figure 9C:
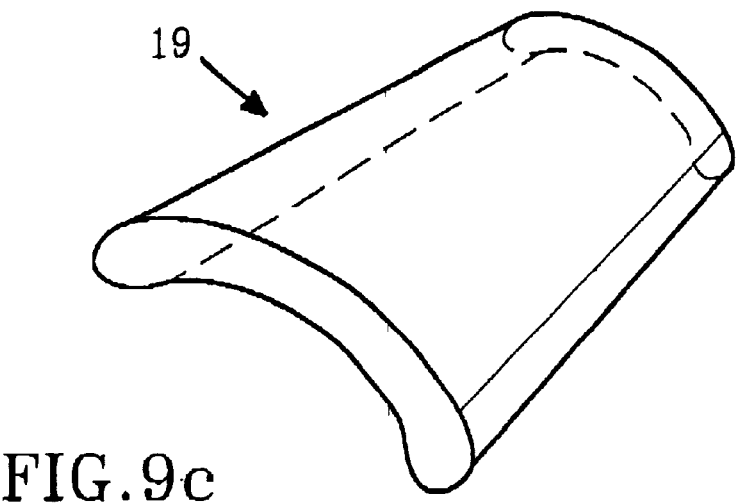

In FIGS. 9a–c there are shown some variants of funnels 19 with different cross sectional shape. The funnel shown in FIG. 9a is essentially straight-edged, tapers relatively quickly and leads into a long, narrow rectangular nib 19a. With this funnel the fibers will be evenly distributed over the entire width. The space within the funnel 19 should be only somewhat larger than the desired material volume. The nib 19a gives the fibers time to stabilize in an even layer.

In FIG. 9b there is shown a funnel having a D-shaped cross section and with this it will be possible to have an increased concentration of fibers in the mid portion as compared to the edge portions. If the material web is refracted over the convex surface when the fibers are led into and out of the funnel there will be a shorter way for the fibers to pass at the centre of the funnel, and by this there will be an increased concentration of fibers at the centre of the material web. The fiber distribution can be controlled by the ovality and "brytningsgrad" at the entrance and exit of the funnel. The material web can at the exit of the funnel either be led straight forwards or be refracted upwards or downwards, which in turn can effect the fiber distribution.

In FIG. 9c there is shown a funnel that is curved in the cross direction and where the material web is led over the concave surface and the fibers by that is guided out toward the edges, at which there is obtained an increased fiber concentration along the edges of the material web. The fiber distribution can be guided by the convexity and degree of refraction at the entrance and the exit.

Figure 9D:
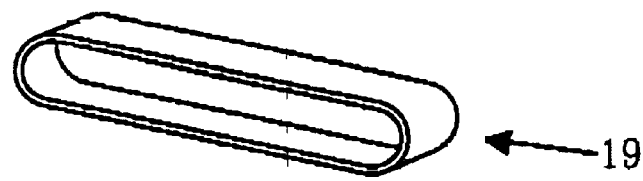

In FIG. 9d there is shown a guiding device in the form of an oval ring 19, i e it has an essentially shorter length than the funnels shown in FIGS. 9a–c.

The folding device 17 is not always necessary, only if the material web is uneven and needs to be evened. An uneven material web may also be sufficiently even by passing it through two or more funnels or rings 19.

Immediatley after the exit form the funnel 19 the material web is fed towards the bonding station 20, which in the embodiment shown consists of en ultrasonic welding device. This comprises an ultrasonic horn 21 arranged just opposite a pattern roll 22 (FIG. 10). The feeding of the material web towards the ultrasonic welding device as well as the web tension of the material web 15 is of importance for the bonding of the material web in a controlled way. The problems which may occur if the feeding of the material web to the ultrasonic welding device is not correctly made is that there will be a risk that:

the material web will be torn apart during welding at a too high stretching of the material;

the material will have different degrees of stretching on the upper and lower sides due to that the fibers do not have the same conditions in the passage through the welding device;

the material web will bulge in front of the ultrasonic horn 21 which results in an uneven feeding of the material to the ultrasonic welding device.

By changing the feeding direction of the material web in connection with the entrance into and/or exit out of the guiding device, as is shown in FIG. 10 and described above the fiber distribution in the cross direction of the material web is controlled.

The funnel 19 or other type of guiding device for forming the material web in the cross direction is however not always necessary, and in these cases the material web is after through-air blowing in the ejector 18 fed directly into the bonding station 20 as is shown in FIG. 6.

What is claimed is:

1. A method of producing an absorbent article, comprising the steps of:

taking at least one bundle of continuous fibers defining a tow, opening the tow and separating the continuous fibers and evening the tow to a fibrous layer having a desired fiber distribution;

bonding the fibrous layer by thermal bonding in a bonding pattern having a plurality of bonded regions, wherein each of the bonded regions extend obliquely or transversely across a longitudinal direction of a plurality of the continuous fibers so that the plurality of the continuous fibers are bonded to each other by each of the bonded regions but where the continuous fibers otherwise are substantially unbonded to each other and wherein a thickness of the fibrous layer is reduced in an area of the bonded regions; and incorporating the fibrous layer in an absorbent article.

2. Method as claimed in claim 1, further comprising bringing air to pass through the opened and separated fibrous layer.

3. Method as claimed in claim 2, wherein the air is brought to pass essentially in the longitudinal direction of, in the transverse direction of and/or obliquely across the fiber direction.

4. Method as claimed in claim 3, wherein the fibrous layer is passed through an ejector.

5. Method as claimed in claim 1, wherein the opened and separated fibrous layer is folded one or more times in its longitudinal direction.

6. Method as claimed in claim 5, wherein the fibrous layer is bonded in a desired bonding pattern immediately after exit from the guiding device.

7. Method as claimed in claim 1, wherein the opened and separated fibrous layer is fed into a guiding device having a certain cross-sectional shape designed to control the fibers distribution in the cross direction of the layer.

8. Method as claimed in claim 7, wherein the feeding direction of the fibrous layer is changed in connection with the entrance into and/or the exit out from the guiding device in order to provide a guiding of the fiber distribution in the cross direction of the layer.

9. Method as claimed in claim 1, further comprising opening the tow and separating the fibers by passing the tow through roll nips while simultaneously stretching the fibers.

10. Method as claimed in claim 1, wherein the bonding is made by means of an ultrasonic welding device comprising a horn and a pattern roll, at which the pattern roll has protruded parts providing a desired bonding pattern, said protruded parts on their tops being provided with an uneven surface in the form of grooves.

11. Method as claimed in claim 1, wherein the bonding is made by means of an ultrasonic welding device comprising a horn and a pattern roll, said horn having an uneven surface in the form of grooves.

12. Method as claimed in claim 1, wherein the fibrous layer is laminated to a nonwoven material or plastic film over at least a part of its width.

13. The method of claim 1, further comprising the step of providing an absorbent core in the absorbent article, the fibrous material layer being disposed on top of the absorbent core.

14. Method as claimed in claim 1, wherein the absorbent article is a diaper.

15. Method as claimed in claim 1, wherein the absorbent article is a pant diaper.

16. Method as claimed in claim 1, wherein the absorbent article is an incontinence guard.

17. Method as claimed in claim 1, wherein the absorbent article is a sanitary napkin.

18. Method as claimed in claim 1, wherein said bonding step thereby increases an acquisition rate of the fibrous material layer.

19. The method as claimed in claim 1, wherein the fibrous material layer incorporated in an absorbent article is an acquisition layer positioned between a topsheet and an absorbent body.

20. The method as claimed in claim 1, wherein the bonded regions comprise diagonally extending lines.

21. The method as claimed in claim 1, wherein the bonding step results in at least a portion of the plurality of bonded regions overlapping each other as seen across the longitudinal direction of the continuous fibers.

22. The method as claimed in claim 1, wherein the bonding step results in bonding a main part of the continuous fibers at least at some part of their length.

23. The method of claim 1, wherein the reduction in the thickness produces a thickness gradient across the absorbent article.

* * * * *